United States Patent
Anderson et al.

(10) Patent No.: US 8,663,337 B2
(45) Date of Patent: Mar. 4, 2014

(54) PROCESS FOR FORMING A CERAMIC LAYER

(75) Inventors: Jeffrey P. Anderson, Warsaw, IN (US); Oludele O. Popoola, Granger, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/413,145

(22) Filed: Mar. 6, 2012

(65) Prior Publication Data

US 2012/0165953 A1 Jun. 28, 2012

Related U.S. Application Data

(62) Division of application No. 11/764,585, filed on Jun. 18, 2007, now Pat. No. 8,133,553.

(51) Int. Cl.
- *A61F 2/28* (2006.01)
- *A61L 33/00* (2006.01)
- *B05D 3/00* (2006.01)
- *A61K 6/083* (2006.01)
- *A61L 27/32* (2006.01)

(52) U.S. Cl.
USPC ..... 623/23.56; 427/2.24; 427/2.26; 427/2.27; 623/16.11

(58) Field of Classification Search
USPC ................................... 623/23.56
See application file for complete search history.

(56) References Cited

U.S. PATENT DOCUMENTS

| | | | |
|---|---|---|---|
| 2,987,352 A | 6/1961 | Watson | |
| 3,605,123 A | 9/1971 | Hahn | |
| 3,643,658 A | 2/1972 | Steinemenan | |
| 3,677,795 A | 7/1972 | Bokros et al. | |
| 4,004,064 A | 1/1977 | Kessler | |
| 4,145,764 A | 3/1979 | Suzuki et al. | |
| 4,487,808 A | 12/1984 | Lambert | |
| 4,563,489 A | 1/1986 | Urist | |

(Continued)

FOREIGN PATENT DOCUMENTS

| | | |
|---|---|---|
| CH | 657519 A5 | 9/1986 |
| DE | 4106971 C1 | 3/1992 |

(Continued)

OTHER PUBLICATIONS

"U.S. Appl. No. 11/764,585, Applicant's Summary of Examiner Interview filed Dec. 1, 2011", 2 pgs.

(Continued)

*Primary Examiner* — Bruce E Snow
*Assistant Examiner* — Brian Dukert
(74) *Attorney, Agent, or Firm* — Schwegman, Lundberg & Woessner, P.A.

(57) ABSTRACT

A process for forming a ceramic layer comprising a compound of a metal on a deposition surface of a workpiece comprises providing a reactive gas, selecting the amounts of a vapor of the metal and ions of the metal relative to each other, generating the metal vapor, and projecting an ion beam of the metal ions. The metal vapor, the metal ions, and the reactive gas form the ceramic layer with a desired structure. The process may include the step of controlling a deposition surface temperature. In one embodiment, the metal vapor comprises zirconium vapor and the ion beam comprises zirconium ions. The relative amounts of the zirconium vapor and the zirconium ions are selected to form a zirconia ceramic layer on the deposition surface. The zirconia may have multiple crystal phases that are formed according to a predetermined ratio.

17 Claims, 4 Drawing Sheets

(56) References Cited

U.S. PATENT DOCUMENTS

| | | |
|---|---|---|
| 4,570,271 A | 2/1986 | Sump |
| 4,671,824 A | 6/1987 | Haygarth |
| 4,713,076 A | 12/1987 | Draenert |
| 4,923,471 A | 5/1990 | Morgan |
| 5,037,438 A * | 8/1991 | Davidson ............... 623/22.15 |
| 5,084,050 A | 1/1992 | Draenert |
| 5,178,201 A | 1/1993 | Ahlers |
| 5,185,215 A * | 2/1993 | Adams et al. ............... 428/545 |
| 5,198,308 A | 3/1993 | Shetty et al. |
| 5,258,022 A | 11/1993 | Davidson |
| 5,282,861 A | 2/1994 | Kaplan |
| 5,302,414 A | 4/1994 | Aklhimov et al. |
| 5,316,594 A | 5/1994 | Kemp |
| 5,323,954 A | 6/1994 | Shetty et al. |
| 5,324,009 A | 6/1994 | Kemp |
| 5,330,826 A | 7/1994 | Taylor et al. |
| 5,383,934 A | 1/1995 | Armini et al. |
| 5,397,796 A | 3/1995 | Zoller et al. |
| 5,399,207 A | 3/1995 | Kemp |
| 5,409,703 A | 4/1995 | McAnalley et al. |
| 5,447,724 A | 9/1995 | Helmus et al. |
| 5,458,653 A | 10/1995 | Davidson |
| 5,464,440 A | 11/1995 | Johansson |
| 5,470,829 A | 11/1995 | Prisell et al. |
| 5,492,697 A | 2/1996 | Boyan et al. |
| 5,509,899 A | 4/1996 | Fan et al. |
| 5,529,914 A | 6/1996 | Hubbell et al. |
| 5,534,524 A | 7/1996 | Bonewald et al. |
| 5,535,810 A | 7/1996 | Compton et al. |
| 5,543,441 A | 8/1996 | Rhee et al. |
| 5,550,178 A | 8/1996 | Desai et al. |
| 5,554,594 A | 9/1996 | Zoller et al. |
| 5,565,407 A | 10/1996 | Southard |
| 5,569,463 A | 10/1996 | Helmus et al. |
| 5,573,934 A | 11/1996 | Hubbell et al. |
| 5,612,052 A | 3/1997 | Shalaby |
| 5,631,011 A | 5/1997 | Wadstrom |
| 5,631,142 A | 5/1997 | Wang et al. |
| 5,658,334 A | 8/1997 | Caldarise et al. |
| 5,658,935 A | 8/1997 | Klingler et al. |
| 5,665,118 A | 9/1997 | LaSalle et al. |
| 5,688,855 A | 11/1997 | Stoy et al. |
| 5,713,410 A | 2/1998 | LaSalle et al. |
| 5,714,159 A | 2/1998 | Shalaby |
| 5,736,160 A | 4/1998 | Ringeisen et al. |
| 5,788,979 A | 8/1998 | Alt et al. |
| 5,801,033 A | 9/1998 | Hubbell et al. |
| 5,824,651 A | 10/1998 | Nanci et al. |
| 5,834,274 A | 11/1998 | Hubbell et al. |
| 5,843,743 A | 12/1998 | Hubbell et al. |
| 5,866,113 A | 2/1999 | Hendriks et al. |
| 5,893,846 A | 4/1999 | Bales et al. |
| 5,925,552 A | 7/1999 | Keogh |
| 5,928,916 A | 7/1999 | Keogh |
| 5,932,299 A | 8/1999 | Katoot |
| 5,947,893 A | 9/1999 | Agrawal et al. |
| 5,980,974 A | 11/1999 | Armini et al. |
| 6,004,943 A | 12/1999 | Shi et al. |
| 6,080,488 A | 6/2000 | Hostettler et al. |
| 6,099,562 A | 8/2000 | Ding et al. |
| 6,110,483 A | 8/2000 | Whitbourne et al. |
| 6,120,536 A | 9/2000 | Ding et al. |
| 6,121,027 A | 9/2000 | Clapper et al. |
| 6,153,252 A | 11/2000 | Hossainy et al. |
| 6,166,173 A | 12/2000 | Mao et al. |
| 6,176,849 B1 | 1/2001 | Yang et al. |
| 6,177,095 B1 | 1/2001 | Sawhney et al. |
| 6,179,817 B1 | 1/2001 | Zhong |
| 6,180,606 B1 | 1/2001 | Chen et al. |
| 6,197,051 B1 | 3/2001 | Zhong |
| 6,238,687 B1 | 5/2001 | Mao et al. |
| 6,254,634 B1 | 7/2001 | Anderson et al. |
| 6,258,121 B1 | 7/2001 | Yang et al. |
| 6,284,305 B1 | 9/2001 | Ding et al. |
| 6,309,660 B1 | 10/2001 | Hsu et al. |
| 6,313,119 B1 | 11/2001 | Peyman et al. |
| 6,316,522 B1 | 11/2001 | Loomis et al. |
| 6,322,797 B1 | 11/2001 | Mao et al. |
| 6,368,658 B1 | 4/2002 | Schwarz et al. |
| 6,395,023 B1 | 5/2002 | Summers |
| 6,395,029 B1 | 5/2002 | Levy |
| 6,410,044 B1 | 6/2002 | Chudzik et al. |
| 6,413,539 B1 | 7/2002 | Shalaby |
| 6,451,373 B1 | 9/2002 | Hossainy et al. |
| 6,455,541 B1 | 9/2002 | Bonewald et al. |
| 6,461,631 B1 | 10/2002 | Dunn et al. |
| 6,486,232 B1 | 11/2002 | Wise et al. |
| 6,492,356 B1 | 12/2002 | Peyman et al. |
| 6,500,481 B1 | 12/2002 | Vanderlaan et al. |
| 6,506,437 B1 | 1/2003 | Harish et al. |
| 6,514,515 B1 | 2/2003 | Williams |
| 6,514,734 B1 | 2/2003 | Clapper et al. |
| 6,528,080 B2 | 3/2003 | Dunn et al. |
| 6,540,746 B1 | 4/2003 | Buhler et al. |
| 6,544,472 B1 | 4/2003 | Compton et al. |
| 6,545,097 B2 | 4/2003 | Pinchuk et al. |
| 6,558,734 B2 | 5/2003 | Koulik et al. |
| 6,596,402 B2 | 7/2003 | Soerens et al. |
| 6,600,010 B2 | 7/2003 | Mao et al. |
| 6,613,088 B1 | 9/2003 | Babizhayev |
| 6,620,194 B2 | 9/2003 | Ding et al. |
| 6,632,446 B1 | 10/2003 | Hubbell et al. |
| 6,656,517 B2 | 12/2003 | Michal |
| 6,669,980 B2 | 12/2003 | Hansen |
| 6,673,385 B1 | 1/2004 | Ding et al. |
| 6,692,790 B2 | 2/2004 | Liu et al. |
| 6,723,350 B2 | 4/2004 | Burrell et al. |
| 6,726,725 B2 | 4/2004 | Hunter et al. |
| 6,730,324 B2 | 5/2004 | Troczynski et al. |
| 6,733,768 B2 | 5/2004 | Hossainy et al. |
| 6,743,521 B2 | 6/2004 | Hubbell et al. |
| 6,746,685 B2 | 6/2004 | Williams |
| 6,749,639 B2 | 6/2004 | Lewallen |
| 6,833,192 B1 | 12/2004 | Caruso et al. |
| 6,833,363 B2 | 12/2004 | Renier et al. |
| 6,855,329 B1 | 2/2005 | Shakesheff et al. |
| 6,866,860 B2 | 3/2005 | Nathan |
| 6,869,445 B1 | 3/2005 | Johnson |
| 6,872,799 B2 | 3/2005 | Nathan |
| 6,881,766 B2 | 4/2005 | Hain |
| 6,899,107 B2 | 5/2005 | Lewandrowski et al. |
| 6,899,731 B2 | 5/2005 | Li et al. |
| 6,921,811 B2 | 7/2005 | Zamora et al. |
| 6,923,986 B2 | 8/2005 | Pathak et al. |
| 6,923,996 B2 | 8/2005 | Epstein et al. |
| 6,945,448 B2 | 9/2005 | Medlin et al. |
| 6,946,443 B2 | 9/2005 | Blanchat et al. |
| 6,967,234 B2 | 11/2005 | Nathan |
| 6,969,400 B2 | 11/2005 | Rhee et al. |
| 6,974,625 B2 | 12/2005 | Hunter et al. |
| 6,986,899 B2 | 1/2006 | Hossainy et al. |
| 6,991,681 B2 | 1/2006 | Yoe |
| 6,991,802 B1 | 1/2006 | Ahola et al. |
| 6,994,883 B2 | 2/2006 | Layrolle et al. |
| 6,998,134 B2 | 2/2006 | Schmidmaier et al. |
| 7,001,421 B2 | 2/2006 | Cheng et al. |
| 7,008,979 B2 | 3/2006 | Schottman et al. |
| 7,112,361 B2 | 9/2006 | Lynn et al. |
| 7,148,209 B2 | 12/2006 | Hoemann et al. |
| 7,157,096 B2 | 1/2007 | Zhang et al. |
| 7,163,715 B1 | 1/2007 | Kramer |
| 7,185,695 B1 | 3/2007 | Santeler |
| 7,186,811 B2 | 3/2007 | Lindholm et al. |
| 7,838,083 B1 | 11/2010 | Youchison et al. |
| 8,133,553 B2 | 3/2012 | Anderson et al. |
| 2002/0018798 A1 | 2/2002 | Sewing et al. |
| 2002/0041899 A1 | 4/2002 | Chudzik et al. |
| 2002/0082552 A1 | 6/2002 | Ding et al. |
| 2002/0084194 A1 | 7/2002 | Redepenning |
| 2002/0087184 A1 | 7/2002 | Eder et al. |
| 2002/0103526 A1 | 8/2002 | Steinke |
| 2002/0111590 A1 | 8/2002 | Davila et al. |
| 2002/0119179 A1 | 8/2002 | Rezania et al. |
| 2002/0120333 A1 | 8/2002 | Keogh et al. |

(56) References Cited

U.S. PATENT DOCUMENTS

| | | |
|---|---|---|
| 2002/0131989 A1 | 9/2002 | Brown et al. |
| 2002/0151617 A1 | 10/2002 | Mao et al. |
| 2002/0165608 A1 | 11/2002 | Llanos et al. |
| 2002/0192182 A1 | 12/2002 | Massia et al. |
| 2003/0004568 A1 | 1/2003 | Ken et al. |
| 2003/0007991 A1 | 1/2003 | Masters |
| 2003/0036794 A1 | 2/2003 | Ragheb et al. |
| 2003/0083740 A1 | 5/2003 | Pathak |
| 2003/0088307 A1 | 5/2003 | Shulze et al. |
| 2003/0099762 A1 | 5/2003 | Zhang et al. |
| 2003/0113478 A1 | 6/2003 | Dang et al. |
| 2003/0114937 A1 | 6/2003 | Leatherbury et al. |
| 2003/0117579 A1 | 6/2003 | Morris et al. |
| 2003/0118692 A1 | 6/2003 | Wang et al. |
| 2003/0124172 A1 | 7/2003 | Lopez Lacomba et al. |
| 2003/0124368 A1 | 7/2003 | Lynn et al. |
| 2003/0129130 A1 | 7/2003 | Guire et al. |
| 2003/0157030 A1 | 8/2003 | Davis et al. |
| 2003/0185752 A1 | 10/2003 | Nathan et al. |
| 2003/0219562 A1 | 11/2003 | Rypacek et al. |
| 2003/0228364 A1 | 12/2003 | Nathan |
| 2003/0229393 A1 | 12/2003 | Kutryk et al. |
| 2004/0033249 A1 | 2/2004 | Sewing et al. |
| 2004/0039441 A1 | 2/2004 | Rowland et al. |
| 2004/0044404 A1 | 3/2004 | Stucke et al. |
| 2004/0049265 A1 | 3/2004 | Ding et al. |
| 2004/0051201 A1 | 3/2004 | Greenhalgh et al. |
| 2004/0063654 A1 | 4/2004 | Davis et al. |
| 2004/0081745 A1 | 4/2004 | Hansen |
| 2004/0086493 A1 | 5/2004 | Hubbell et al. |
| 2004/0086543 A1 | 5/2004 | Keogh et al. |
| 2004/0091462 A1 | 5/2004 | Lin et al. |
| 2004/0091603 A1 | 5/2004 | Priewe |
| 2004/0093080 A1 | 5/2004 | Helmus et al. |
| 2004/0106985 A1 | 6/2004 | Jang et al. |
| 2004/0109892 A1 | 6/2004 | Shalaby |
| 2004/0117007 A1 | 6/2004 | Whitbourne et al. |
| 2004/0120982 A1 | 6/2004 | Diana et al. |
| 2004/0126405 A1 | 7/2004 | Sahatjian et al. |
| 2004/0133271 A1 | 7/2004 | Jang |
| 2004/0137066 A1 | 7/2004 | Jayaraman |
| 2004/0138695 A1 | 7/2004 | Li et al. |
| 2004/0147999 A1 | 7/2004 | Udipi et al. |
| 2004/0157073 A1 | 8/2004 | Burrell et al. |
| 2004/0170752 A1 | 9/2004 | Luthra et al. |
| 2004/0172121 A1 | 9/2004 | Eidenschink et al. |
| 2004/0185086 A1 | 9/2004 | Massia et al. |
| 2004/0215313 A1 | 10/2004 | Cheng |
| 2004/0215336 A1 | 10/2004 | Udipi et al. |
| 2004/0241202 A1 | 12/2004 | Chluba et al. |
| 2004/0241234 A1 | 12/2004 | Vilkov |
| 2005/0025752 A1 | 2/2005 | Kutryk et al. |
| 2005/0025799 A1 | 2/2005 | Hossainy et al. |
| 2005/0031689 A1 | 2/2005 | Shults et al. |
| 2005/0031793 A1 | 2/2005 | Moeller et al. |
| 2005/0036946 A1 | 2/2005 | Pathak et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0079200 A1 | 4/2005 | Rathenow et al. |
| 2005/0084515 A1 | 4/2005 | Udipi et al. |
| 2005/0085605 A1 | 4/2005 | Nathan |
| 2005/0095267 A1 | 5/2005 | Campbell et al. |
| 2005/0101692 A1 | 5/2005 | Sohier et al. |
| 2005/0102035 A1 | 5/2005 | Grundei |
| 2005/0106204 A1 | 5/2005 | Hossainy et al. |
| 2005/0112170 A1 | 5/2005 | Hossainy et al. |
| 2005/0112172 A1 | 5/2005 | Pacetti |
| 2005/0129731 A1 | 6/2005 | Horres et al. |
| 2005/0142393 A1 | 6/2005 | Boutwell et al. |
| 2005/0147647 A1 | 7/2005 | Glauser et al. |
| 2005/0149171 A1 | 7/2005 | McCullagh et al. |
| 2005/0152955 A1 | 7/2005 | Akhave et al. |
| 2005/0153429 A1 | 7/2005 | Liebmann-Vinson et al. |
| 2005/0154450 A1 | 7/2005 | Larson et al. |
| 2005/0158359 A1 | 7/2005 | Epstein et al. |
| 2005/0159746 A1 | 7/2005 | Grob et al. |
| 2005/0165128 A1 | 7/2005 | Cohn et al. |
| 2005/0169882 A1 | 8/2005 | Lowe et al. |
| 2005/0169969 A1 | 8/2005 | Li et al. |
| 2005/0180919 A1 | 8/2005 | Tedeschi |
| 2005/0183259 A1 | 8/2005 | Eidenschink et al. |
| 2005/0187376 A1 | 8/2005 | Pacetti |
| 2005/0187602 A1 | 8/2005 | Eidenschink |
| 2005/0187611 A1 | 8/2005 | Ding et al. |
| 2005/0191333 A1 | 9/2005 | Hsu |
| 2005/0208093 A1 | 9/2005 | Glauser et al. |
| 2005/0208100 A1 | 9/2005 | Weber et al. |
| 2005/0208200 A1 | 9/2005 | Ding et al. |
| 2005/0214339 A1 | 9/2005 | Tang et al. |
| 2005/0214916 A1 | 9/2005 | Absar et al. |
| 2005/0215722 A1 | 9/2005 | Pinchunk et al. |
| 2005/0220837 A1 | 10/2005 | Disegi et al. |
| 2005/0220839 A1 | 10/2005 | DeWitt et al. |
| 2005/0220840 A1 | 10/2005 | DeWitt et al. |
| 2005/0220841 A1 | 10/2005 | DeWitt et al. |
| 2005/0220842 A1 | 10/2005 | DeWitt et al. |
| 2005/0220843 A1 | 10/2005 | DeWitt et al. |
| 2005/0244363 A1 | 11/2005 | Hossainy et al. |
| 2005/0244453 A1 | 11/2005 | Stucke et al. |
| 2005/0244459 A1 | 11/2005 | DeWitt et al. |
| 2005/0245637 A1 | 11/2005 | Hossainy et al. |
| 2005/0251250 A1 | 11/2005 | Verhoeven et al. |
| 2005/0255142 A1 | 11/2005 | Chudzik et al. |
| 2005/0266038 A1 | 12/2005 | Glauser et al. |
| 2005/0266077 A1 | 12/2005 | Royer |
| 2005/0271700 A1 | 12/2005 | DesNoyer et al. |
| 2005/0271701 A1 | 12/2005 | Cottone, Jr. et al. |
| 2005/0274478 A1 | 12/2005 | Verner et al. |
| 2005/0283224 A1 | 12/2005 | King |
| 2005/0288229 A1 | 12/2005 | Sindrey et al. |
| 2006/0003008 A1 | 1/2006 | Gibson et al. |
| 2006/0008500 A1 | 1/2006 | Chavan et al. |
| 2006/0009839 A1 | 1/2006 | Tan |
| 2006/0013850 A1 | 1/2006 | Domb |
| 2006/0018948 A1 | 1/2006 | Guire et al. |
| 2006/0025848 A1 | 2/2006 | Weber et al. |
| 2006/0035854 A1 | 2/2006 | Goldstein et al. |
| 2006/0036311 A1 | 2/2006 | Nakayama et al. |
| 2006/0036316 A1 | 2/2006 | Zeltinger et al. |
| 2006/0039947 A1 | 2/2006 | Schmidmaier et al. |
| 2006/0039950 A1 | 2/2006 | Zhou et al. |
| 2006/0045901 A1 | 3/2006 | Weber |
| 2006/0051978 A1 | 3/2006 | Li et al. |
| 2006/0057277 A1 | 3/2006 | Chappa |
| 2006/0067969 A1 | 3/2006 | Lu et al. |
| 2006/0093646 A1 | 5/2006 | Cima et al. |
| 2006/0105018 A1 | 5/2006 | Epstein et al. |
| 2006/0121081 A1 | 6/2006 | Labrecque et al. |
| 2006/0135652 A1 | 6/2006 | Kasseh et al. |
| 2006/0165754 A1 | 7/2006 | Ranade |
| 2006/0188541 A1 | 8/2006 | Richelsoph et al. |
| 2006/0198868 A1 | 9/2006 | DeWitt et al. |
| 2006/0204536 A1 | 9/2006 | Shults et al. |
| 2006/0204542 A1 | 9/2006 | Zhang et al. |
| 2006/0210598 A1 | 9/2006 | Evans et al. |
| 2006/0210602 A1 | 9/2006 | Sehl et al. |
| 2006/0216772 A1 | 9/2006 | Grinstaff et al. |
| 2006/0222681 A1 | 10/2006 | Richard |
| 2006/0222756 A1 | 10/2006 | Davila et al. |
| 2006/0233801 A1 | 10/2006 | Brunkow et al. |
| 2006/0233841 A1 | 10/2006 | Brodbeck et al. |
| 2006/0233941 A1 | 10/2006 | Olson |
| 2006/0233944 A1 | 10/2006 | Popoola et al. |
| 2006/0240063 A9 | 10/2006 | Hunter et al. |
| 2006/0246103 A1 | 11/2006 | Ralph et al. |
| 2006/0246105 A1 | 11/2006 | Molz et al. |
| 2006/0246110 A1 | 11/2006 | Brandon et al. |
| 2006/0247793 A1 | 11/2006 | Trieu et al. |
| 2006/0251824 A1 | 11/2006 | Boulais et al. |
| 2006/0252981 A1 | 11/2006 | Matsuda et al. |
| 2006/0257377 A1 | 11/2006 | Atala et al. |
| 2006/0263830 A1 | 11/2006 | Grinstaff et al. |
| 2006/0263831 A1 | 11/2006 | Grinstaff et al. |

(56) References Cited

U.S. PATENT DOCUMENTS

| | | |
|---|---|---|
| 2006/0264531 A1 | 11/2006 | Zhao |
| 2006/0286064 A1 | 12/2006 | Turnell et al. |
| 2006/0286071 A1 | 12/2006 | Epstein et al. |
| 2006/0293406 A1 | 12/2006 | Bennet et al. |
| 2007/0016163 A1 | 1/2007 | Santini, Jr. et al. |
| 2007/0020308 A1 | 1/2007 | Richard et al. |
| 2007/0020469 A1 | 1/2007 | Wood et al. |
| 2007/0026043 A1 | 2/2007 | Guan et al. |
| 2007/0032882 A1 | 2/2007 | Lodhi et al. |
| 2007/0037737 A1 | 2/2007 | Hoemann et al. |
| 2007/0038300 A1 | 2/2007 | Bao et al. |
| 2007/0041952 A1 | 2/2007 | Guilak et al. |
| 2007/0042017 A1 | 2/2007 | Kutryk et al. |
| 2007/0043374 A1 | 2/2007 | Evans |
| 2007/0043433 A1 | 2/2007 | Chandrasekaran |
| 2007/0045902 A1 | 3/2007 | Brauker et al. |
| 2007/0048291 A1 | 3/2007 | Mang et al. |
| 2007/0048292 A1 | 3/2007 | Morita et al. |
| 2007/0053963 A1 | 3/2007 | Hotchkiss et al. |
| 2007/0054127 A1 | 3/2007 | Hergenrother et al. |
| 2007/0055095 A1 | 3/2007 | Chu et al. |
| 2007/0055367 A1 | 3/2007 | Kutryk et al. |

FOREIGN PATENT DOCUMENTS

| | | |
|---|---|---|
| DE | 4302167 C1 | 2/1994 |
| EP | 0159089 A1 | 10/1985 |
| EP | 0361896 A2 | 4/1990 |
| EP | 0372662 A2 | 6/1990 |
| EP | 0375127 A1 | 6/1990 |
| EP | 0395187 A2 | 10/1990 |
| EP | 0530804 A1 | 3/1993 |
| EP | 0812931 A1 | 12/1997 |
| EP | 1055743 A1 | 11/2000 |
| EP | 1273303 A1 | 1/2003 |
| EP | 1144018 B1 | 3/2004 |
| EP | 1679088 A2 | 7/2006 |
| EP | 1806155 A2 | 7/2007 |
| EP | 0616814 A1 | 10/2007 |
| FR | 2675694 A1 | 10/1992 |
| WO | WO-8905161 A1 | 6/1989 |
| WO | WO-9015586 A2 | 12/1990 |
| WO | WO-9307835 A1 | 4/1993 |
| WO | WO-9309229 A1 | 5/1993 |
| WO | WO-9628117 A1 | 9/1996 |
| WO | WO-9738649 A1 | 10/1997 |
| WO | WO-0056879 A1 | 9/2000 |
| WO | WO-0064460 A2 | 11/2000 |
| WO | WO-0139680 A1 | 6/2001 |
| WO | WO-0182989 A1 | 11/2001 |
| WO | WO-03077772 A1 | 9/2003 |
| WO | WO-2004002544 A1 | 1/2004 |
| WO | WO-2004071350 A1 | 8/2004 |
| WO | WO-2005120203 A2 | 12/2005 |
| WO | WO-2006033956 A2 | 3/2006 |
| WO | WO-2007014279 A2 | 2/2007 |
| WO | WO-2007038559 A2 | 4/2007 |
| WO | WO-2007053022 A2 | 5/2007 |

OTHER PUBLICATIONS

"U.S. Appl. No. 11/764,585, Examiner Interview Summary mailed Sep. 22, 2011", 3 pgs.

"U.S. Appl. No. 11/764,585, Examiner Interview Summary mailed Oct. 4, 2011", 2 pgs.

"U.S. Appl. No. 11/764,585, Examiner Interview Summary mailed Nov. 2, 2011", 2 pgs.

"U.S. Appl. No. 11/764,585, Final Office Action mailed Nov. 17, 2010", 9 pgs.

"U.S. Appl. No. 11/764,585, Non Final Office Action mailed Jul. 13, 2010", 17 pgs.

"U.S. Appl. No. 11/764,585, Notice of Allowance mailed Nov. 2, 2011", 5 pgs.

"U.S. Appl. No. 11/764,585, Response filed Feb. 17, 2011 to Final Office Action mailed Nov. 17, 2010", 10 pgs.

"U.S. Appl. No. 11/764,585, Response filed Jun. 4, 2010 to Restriction Requirement mailed May 12, 2010", 2 pgs.

"U.S. Appl. No. 11/764,585, Response filed Oct. 13, 2010 to Non Final Office Action mailed Jul. 13, 2010", 16 pgs.

"U.S. Appl. No. 11/764,585, Restriction Requirement mailed May 12, 2010", 5 pgs.

Aleksyniene, Ramune, et al., "Parathyroid Hormone—Possible Future Drug for Orthopedic Surgery", vol. 40(9): Medicina (Kaunas), (2004), 842-849.

Karthikeyan, Jeganathan, "Cold Spray Technology, Advanced Materials & Processes", ASB Industries, (Mar. 2005), 33-35.

Morris, Carol D, et al., "Bisphosphonates in Orthopaedic Surgery", The Journal of Bone & Joint Surgery Am. 87, (Jul. 2005), 1609-1618.

Pavoor, Prem V, et al., "Wear Reduction of Orthopaedic Bearing Surfaces Using Polyelectrolyte Multilayer Nanocoatings", Biomaterials, 27, (2006), 1527-1533.

Piconi, C, "Zirconia as a ceramic biomaterial", Biomaterials 20, (1999), 1-25.

Termaat, M. F, et al., "Bone Morphogenetic Proteins. Development and Clinical Efficacy in the Treatment of Fractures and Bone Defects", The Journal of Bone & Joint Surgery Am. 87, (Jun. 2005), 1366-1378.

Uhthoff, Hans K, et al., "Internal Plate Fixation of Fractures: Short History and Recent Developments", 11 The Japanese Orthopaedic Association, Japan, (2006), 118-126.

\* cited by examiner

US 8,663,337 B2

PROCESS FOR FORMING A CERAMIC LAYER

CROSS-REFERENCE TO RELATED APPLICATION

This application is a divisional of and claims the benefit of priority under 35 U.S.C. §120 to Jeffrey P. Anderson et al., U.S. patent application Ser. No. 11/764,585, entitled "PROCESS FOR FORMING A CERAMIC LAYER," filed Jun. 18, 2007, which is incorporated herein by reference in its entirety.

FIELD OF THE INVENTION

This invention relates to processes for forming ceramic layers, and, more particularly, to a process for forming a ceramic layer having a desired structure with a predetermined ratio of crystal phases.

BACKGROUND OF THE INVENTION

Ion beam assisted deposition (IBAD) is a process used to deposit thin, adherent coatings onto a surface of a substrate. In this process, the substrate is placed into a vacuum chamber and a vapor and an ion beam are simultaneously used to deposit the thin coating onto the substrate. Ion beam assisted deposition has been used to deposit many different materials, including, for example, zirconium dioxide.

Zirconium dioxide or zirconia has found application on orthopedic implants. Zirconia exhibits many of the preferred and desired attributes for use in vivo. For example, zirconia is biologically inert, hard, and can be formed as a smooth film on an articular surface of an orthopedic implant. Unfortunately, the use of zirconia is not without difficulty.

One difficulty is that zirconia, like many other oxide and nonoxide ceramics, has multiple phases. Zirconia has a monoclinic phase, a tetragonal phase, and a cubic phase. In particular, the difficulty with zirconia arises due to a volume expansion that a zirconia unit cell undergoes when it transforms from tetragonal to monoclinic. The volume expansion is approximately 4%. When zirconia transforms, the volume expansion results in an enormous stress increase within a product made of zirconia. In fact, the stresses that form in bulk components of pure zirconia will often cause spontaneous catastrophic failure of the component. In other applications, particularly in orthopedic implant applications, the phase transformation may result in surface roughening as isolated pockets of tetragonal zirconia transform into monoclinic zirconia, essentially causing the surface to buckle outward as it attempts to expand. Surface roughening on articular surfaces is unacceptable.

Therefore, what is needed in the art is a process for forming a ceramic layer where a particular crystal structure of the ceramic layer may be selected. In addition, what is needed in the art is a process that permits selection or adjustment of the relative amounts of the constituents according to a relationship between the constituents and the ceramic layer such that the ceramic layer is formed with a desired structure having a predetermined ratio of two or more crystal structures. Furthermore, what is needed is a process for forming a zirconia ceramic layer having a desired structure comprising two or more crystal phases, but that does not roughen due to tetragonal to monoclinic zirconia transformation.

SUMMARY OF THE INVENTION

The present invention provides a process for forming a ceramic layer comprising a compound of a metal on a deposition surface of a workpiece. An initial step of the process includes providing a reactive gas in fluid communication with the deposition surface. The process includes generating a vapor of the metal in fluid communication with the deposition surface. The process also includes projecting an ion beam comprising a plurality of ions of the metal on to the deposition surface. In addition, the process includes selecting an amount of the metal vapor relative to an amount of the metal ions. The process may include adjusting the ratio of the metal vapor to the metal ions. In summary, the deposition surface is in fluid communication with the reactive gas, the metal vapor, and the metal ions, which react at the selected amounts to form the ceramic layer with a desired structure on the deposition surface.

In another embodiment, the ceramic layer may comprise zirconia and the desired structure may be tetragonal, monoclinic, or cubic zirconia. In another embodiment of the invention, the desired structure may be formed in a predetermined ratio of at least two crystal phases by selecting the ratio of a zirconium vapor to a plurality of zirconium ions.

In another embodiment the workpiece is an orthopedic implant. The zirconia layer may be comprised of monoclinic, tetragonal, or cubic phases or a combination thereof formed on the orthopedic implant. In yet another embodiment, the zirconia layer may be formed in a predetermined ratio of the monoclinic phase to the tetragonal phase such that the monoclinic to tetragonal phase transformation is suppressed.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1A:
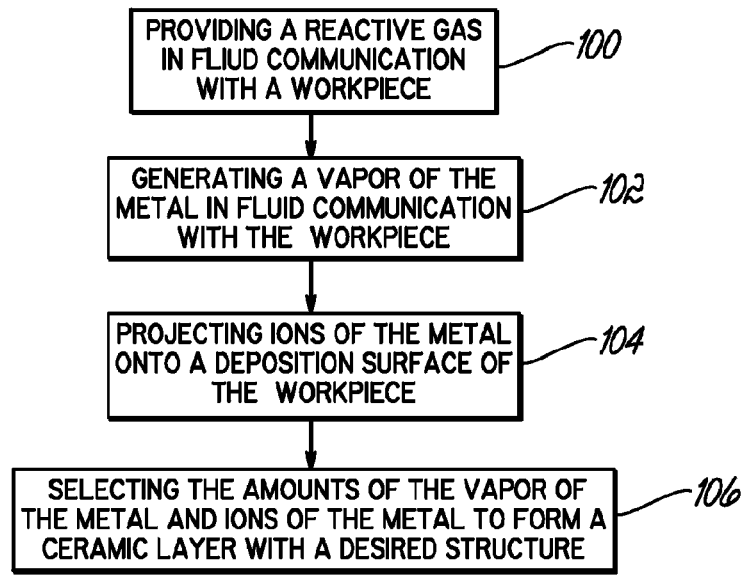
FIG. 1A is a process flow diagram of one embodiment of the process of the present invention.
Figure 1B:
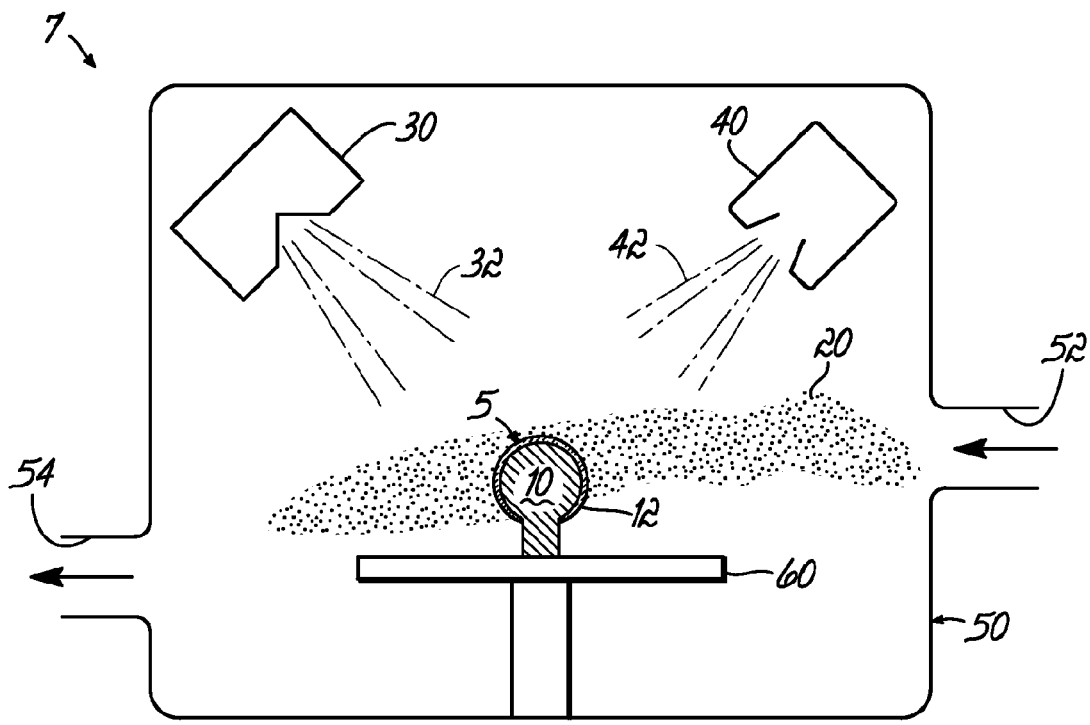
FIG. 1B is an illustration of one embodiment of the process showing formation of a ceramic layer on a workpiece.

One embodiment of a process for forming a ceramic layer 5 comprising a compound of a metal is illustrated by the process flow diagram of FIG. 1A and an apparatus 7 depicted in FIG. 1B. In an initial step of the process in 100, a workpiece 10 is positioned in a chamber 50 of the apparatus 7 and a reactive gas 20 is provided in fluid communication with a deposition surface 12 of the workpiece 10. The process further includes using an evaporator 30 to generate a vapor 32 of the metal and direct it to the workpiece 10, in 102, as depicted in FIG. 1B. The process further includes using an ion source 40 to form ions 42 of the metal. The metal ions 42 are projected, in 104, onto the deposition surface 12, generally in the form of an ion beam. The process further includes selecting the amount of the metal vapor 32 relative to the amount of the metal ions 42 in 106. The deposition surface 12 is thus exposed to the reactive gas 20, the metal vapor 32, and the metal ions 42, which react at selected amounts to form the ceramic layer 5 on the deposition surface 12. The process is not limited to the order as described herein. That is, the steps may be performed in other orders, including simultaneously.

In one embodiment, the process may also include adjusting the ratio of the metal vapor 32 to the metal ions 42 to deposit the ceramic layer 5 with another desired structure. Thus, in accordance with the inventive process, multiple desired structures may be interwoven or layered on the deposition surface 12 by adjusting the ratio of the metal vapor 32 to the metal ions 42 while forming the ceramic layer 5.

In another embodiment, the workpiece 10 and the reactive gas 20 are contained within the chamber 50 and the pressure, the flow rate, and the constituents of the reactive gas 20 are controlled through a supply port 52. The chamber 50 may also have a vacuum port 54 in fluid communication with a vacuum system (not shown) for reducing the pressure inside the chamber 50 prior to both generating the metal vapor 32 and forming the metal ions 42.

Selecting and adjusting the ratio of the metal vapor 32 to the metal ions 42, refers to choosing the ratio according to a relationship between the ratio of the metal vapor 32 to the metal ions 42 and the desired structure of the ceramic layers. The relationship being identified by prior variation of the ratio and quantification of the desired structure formed with each variation. For example, variations in the ratio of the metal vapor 32 to the metal ions 42 in conjunction with the reactive gas 20 are used to form a ceramic layer 5. The desired structure of the ceramic layer 5 for those variations is then quantified. The relationship between the ratio and the desired structure is thus established. Therefore, subsequent selection or adjustment of the ratio of the metal vapor 32 to the metal ions 42 forms the ceramic layer 5 having the desired structure. As the term is used herein, the desired structure is a crystal phase or phases deposited by the reaction of the metal vapor 32 and metal ions 42 and the reactive gas 20.

In one embodiment, the relationship between the ratio of the metal vapor 32 to the metal ions 42 is one that deposits a ceramic layer 5 having a desired structure containing at least two crystal phases. Furthermore, those crystal phases may be formed in a predetermined ratio. In other words, the amount of each crystal phase may be predicted. For example, the predetermined ratio may be represented by a volume of a first crystal phase to a volume of a second crystal phase. One skilled in the art will observe that adjusting or selecting another ratio of the metal vapor 32 to the metal ions 42 may produce a second ratio of the volumes of the first and second crystal phases. Therefore, the invention may permit layering multiple desired structures each having differing volumes of crystal phases. By way of example and not limitation, the crystal phases may comprise crystal phases for $SiO_2$, $ZrO_2$, $TiO_2$, $As_2O_3$, $CaTiO_3$, $Al_2SiO_5$, BN, ZnS, $FeS_2$, or other ceramic systems with polymorphic characteristics. As one skilled in the art will observe, a reactive gas 20 comprising oxygen will form oxides, while a reactive gas comprising sulfur or nitrogen will form sulfide compounds and nitride compounds, respectively.

Figure 6:
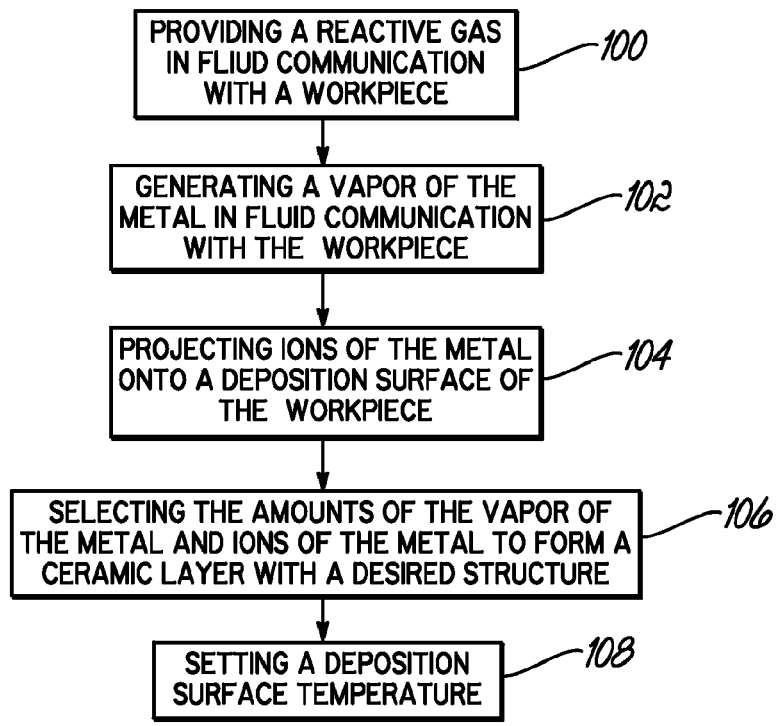
FIG. 6 is a diagram of another embodiment of the process of the present invention.

In another embodiment, the deposition surface 12, illustrated in FIG. 1B, of the workpiece 10 has a deposition surface temperature. With reference now to FIG. 6, the process includes controlling the deposition surface temperature in 108. The deposition surface temperature may influence the desired structure. While FIG. 6 illustrates a process wherein the deposition surface temperature is set following selecting the ratio of the metal vapor 32 to the metal ions 42, the process may alternate between setting the deposition surface temperature and selecting the ratio of the metal vapor 32 to the metal ions 42. Furthermore, setting the deposition surface temperature may occur many times during the process.

In one embodiment of the invention, the impingement of the ion beam may produce a deposition surface temperature greater than room temperature. The deposition surface temperature is less than approximately 1000° C. and may be limited by the workpiece's 10 material properties, such as its melting point. Thus, controlling the deposition surface temperature may require a heating system or a cooling system to attain or maintain the deposition surface temperature. The heating system may be an electrical resistance heating system as is known in the art. With reference to FIG. 1B, the cooling system may be, for example, cooling fluid passing through a work stage 60 supporting the workpiece 10, or the cooling fluid may impinge upon the deposition surface 12 or pass through the workpiece 10 itself. In another embodiment, the deposition surface temperature is greater than approximately 200° C. to substantially prevent water or other tenacious molecules from adhering to the deposition surface 12. In yet another embodiment, the deposition surface temperature is less than approximately 600° C. to avoid inadvertent heat treatment of the workpiece 10 or possible reaction of the workpiece 10 with the metal vapor 32, the metal ions 42, or the reactive gas 20.

In one embodiment of the invention, with reference to FIG. 1B, the metal vapor 32 is zirconium vapor, the metal ions 42 are zirconium ions, and the reactive gas 20 is oxygen. The ceramic layer 5 formed is zirconium dioxide, referred to herein as zirconia. The oxidizing gas 20 may have a pressure of less than approximately $2\times10^{-5}$ ton, or the partial pressure may be sufficient to oxidize substantially all of the zirconium ions 42 in the ion beam and the zirconium vapor 32 to form stoichiometric zirconia, i.e. $ZrO_2$. In any case, the pressure of the oxidizing gas 20 does not substantially interfere with impingement of the ion beam onto the deposition surface 12. A relationship between a ratio of an amount of the zirconium vapor 32 to an amount of the zirconium ions 42 which thereby forms a zirconia ceramic layer 5 is illustrated in FIG. 3 and tabulated in TABLE 1.

With reference to TABLE 1 and FIG. 1B, the "Ion Beam" column tabulates an ion beam voltage and an ion beam current supplied to the ion source 40 for projecting the ion beam of zirconium ions 42 onto the deposition surface 12. The "Evaporator" column lists an evaporator voltage and an evaporator current supplied to the evaporator 30 for generating the zirconium vapor 32. The "PE/PB" column is a calculated ratio of an evaporator power to an ion beam power. Furthermore, the evaporator power (PE) is a product of the evaporator current and the evaporator voltage. Similarly, the ion beam power (PB) is a product of the ion beam current and the ion beam voltage. The "% Monoclinic" column in TABLE 1 represents the volume fraction of the desired structure that is monoclinic zirconia. The % Monoclinic of the desired structure may be determined by x-ray diffraction, as discussed below.

Figure 3:
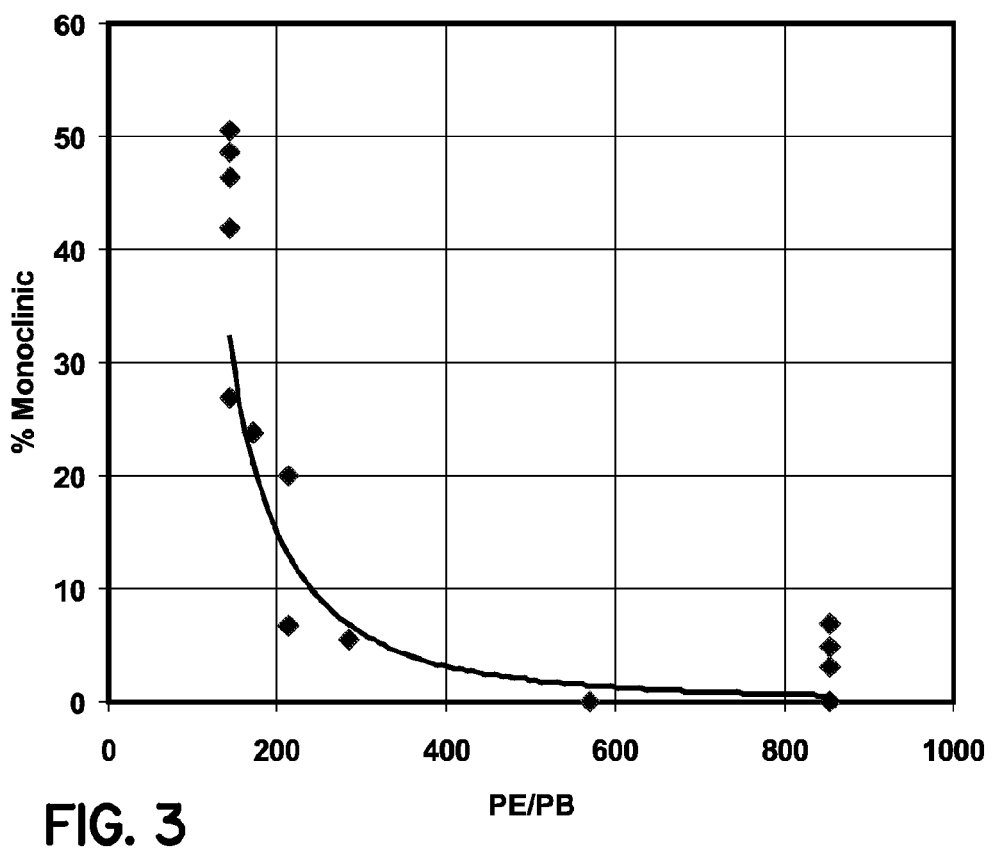
FIG. 3 illustrates a relationship between a ratio of a beam power and an evaporator power (PB/PE) and a desired structure having a predetermined ratio (% Monoclinic)

FIG. 3 is a plot of a portion of the data in TABLE 1. FIG. 3 illustrates a relationship between the ratio of the amount of the zirconium ions 42 to the amount of the zirconium vapor 32 and the desired structure of the zirconia ceramic layer 5. In one embodiment of the process, the evaporator power is related to the amount of the zirconium vapor 32 generated and projected onto the deposition surface 12, and the ion beam power is related to the amount of the zirconium ions 42 that impinge upon the deposition surface 12. As previously discussed, the PE/PB ratio is calculated from the ratio of the evaporator power and the ion beam power. Specifically, the PE/PB and % Monoclinic columns found in TABLE 1 are plotted as abscissa and ordinate in FIG. 3, respectively. Therefore, in general, as the evaporator power is increased relative to the ion beam power, the % Monoclinic in the desired structure approaches zero.

TABLE 1

| Ion Beam | | Evaporator | | | % |
|---|---|---|---|---|---|
| keV | μA | kV | mA | PE/PB | Monoclinic |
| 60 | 500 | 9.5 | 450 | 142.5 | 48.6 |
| 60 | 500 | 9.5 | 450 | 142.5 | 46.3 |
| 60 | 500 | 9.5 | 450 | 142.5 | 41.9 |
| 60 | 500 | 9.5 | 450 | 142.5 | 50.5 |
| 50 | 500 | 9.5 | 450 | 171.0 | 23.8 |
| 40 | 500 | 9.5 | 450 | 213.8 | 20.0 |
| 30 | 250 | 9.5 | 450 | 570.0 | 5.6 |
| 30 | 250 | 9.5 | 450 | 570.0 | 0 |
| 20 | 250 | 9.5 | 450 | 855.0 | 6.9 |
| 20 | 250 | 9.5 | 450 | 855.0 | 4.8 |
| 20 | 250 | 9.5 | 450 | 855.0 | 3.1 |
| 20 | 250 | 9.5 | 450 | 855.0 | 0 |

Therefore, selection of a particular PE/PB ratio will form a zirconia ceramic layer 5. The zirconia ceramic layer 5 may have at least two crystal phases formed in a predetermined ratio. In other words, the zirconia ceramic layer 5 comprises, a monoclinic phase formed according to a known % Monoclinic, as shown in FIG. 3.

In accordance with one embodiment of the present invention, with reference to FIG. 3, by selecting PE/PB ratios of between approximately 50 and approximately 1000, the zirconia ceramic layer 5 is formed with a desired structure comprising two crystal phases, including tetragonal and monoclinic zirconia. The predetermined ratio may be selected as greater than approximately 0 and less than approximately 60% Monoclinic, per FIG. 3.

In another embodiment, during selecting and adjusting, the ion beam power may be adjusted by changing the ion beam current and/or the ion beam voltage. For example, referring to TABLE 1, the ion beam power increases when the ion beam voltage is increased from 30 keV to 40 keV and the ion beam current is increased from 250 μA to 500 μA. Thus, by adjusting the ion beam power or the evaporator power, or both, the PE/PB ratio may be selected to be between approximately 50 and approximately 1000. In another embodiment of the process, the ion beam power is selected such that the PE/PB ratio is between approximately 100 and approximately 900. As one skilled in the art will observe, the PE/PB may depend upon the type of metal vapor 32 and the metal ions 42. Therefore, the evaporator power and ion beam power may vary significantly for other types of metal. In another embodiment of the instant invention, during the step of adjusting the ion beam power, the ion beam voltage is adjusted to between approximately 20 keV and approximately 60 keV, and the ion beam current is adjusted to between approximately 250 μA and approximately 500 μA.

Figure 2:
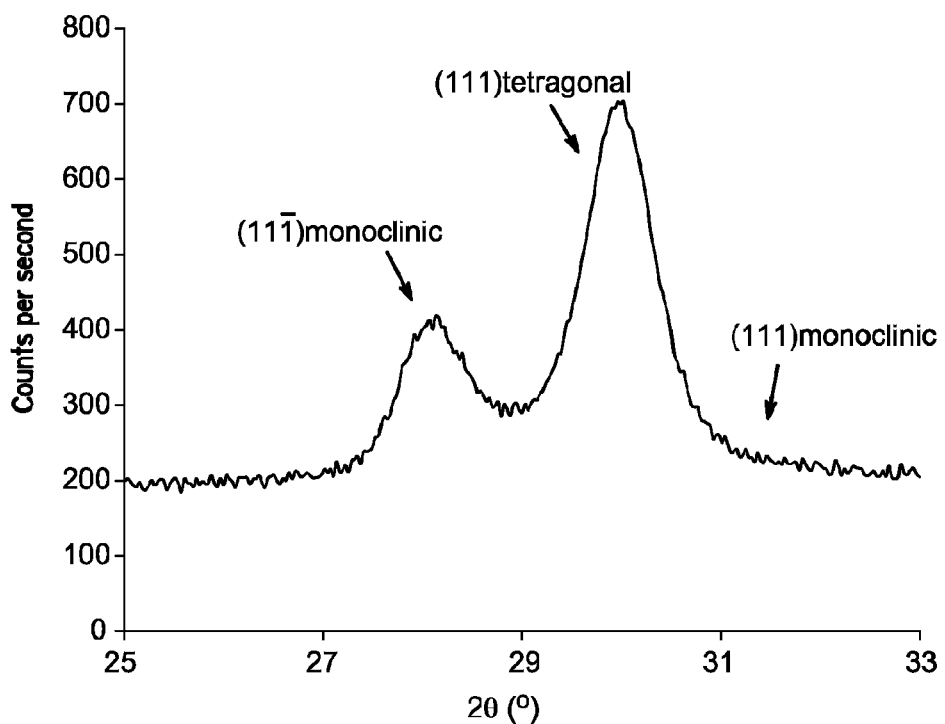
FIG. 2 is an illustration of an x-ray diffraction pattern taken of a ceramic layer comprising zirconia deposited according to one embodiment of the present invention.
Figure 5:
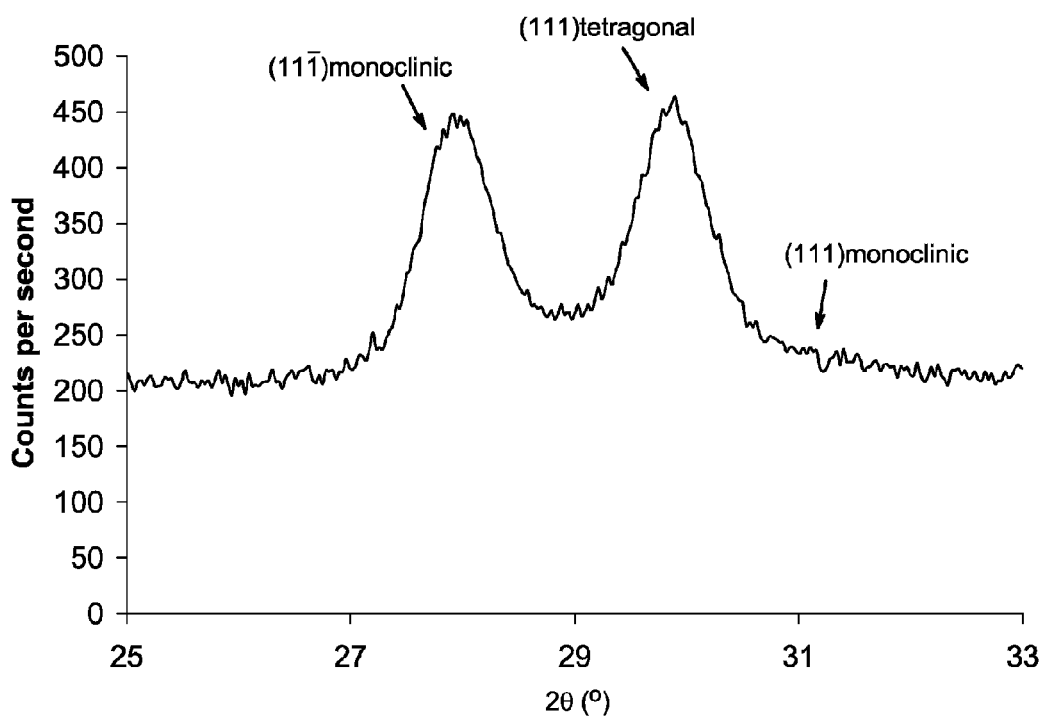
FIG. 5 is another illustration of an x-ray diffraction pattern of a zirconia ceramic layer deposited according to one embodiment of the present invention.

In another embodiment of the present invention, the monoclinic zirconia crystals may form with a preferred crystallographic orientation. FIGS. 2 and 5 are x-ray diffraction patterns of examples of the zirconia ceramic layer 5 formed according to one embodiment of the process. As shown in FIGS. 2 and 5, the (111) tetragonal and the (11$\bar{1}$) monoclinic peaks are present but the (111) monoclinic peak is absent from the x-ray diffraction pattern. As one skilled in the art will appreciate, the presence of the (11$\bar{1}$) monoclinic peak combined with the absence of the (111) monoclinic peak indicates a preferred orientation of the monoclinic crystals on the deposition surface. Therefore, during selecting or adjusting, the crystals may be formed with the preferred crystallographic orientation relative to the deposition surface 12.

Figures 7, 8:
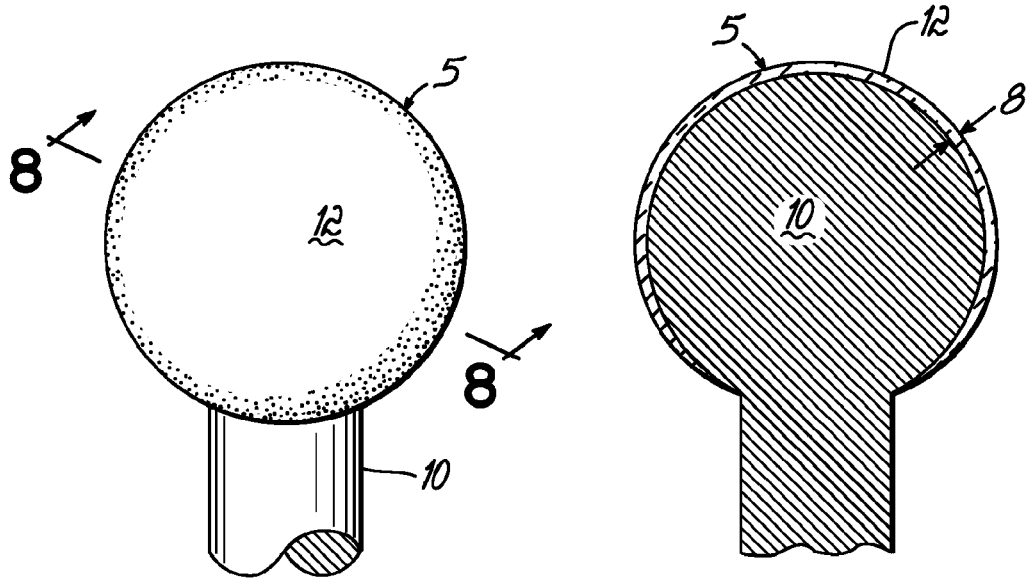
FIG. 7 is a perspective view of one embodiment wherein the workpiece is a femoral hip ball.
FIG. 8 is a cross-sectional view of the embodiment of FIG. 7, taken along section line 8-8.

In yet another embodiment, the predetermined ratio of monoclinic zirconia to tetragonal zirconia is selected to suppress the tetragonal to monoclinic phase transformation. As illustrated in FIGS. 1B, 7 and 8, the workpiece 10 is an orthopedic implant, and the process for forming the zirconia ceramic layer 5 is used to form the desired structure having a predetermined ratio of monoclinic zirconia to tetragonal zirconia on the deposition surface 12 of the orthopedic implant. By way of example and not limitation, the orthopedic implant may be a femoral hip ball implant or femoral knee implant, or other artificial joint. The zirconia ceramic layer 5 is formed as an articular surface on the orthopedic body. The predetermined ratio may be selected to suppress the tetragonal to monoclinic phase transformation such that the articular surface retains its smooth surface and does not roughen during use in vivo. In many of the embodiments, the zirconia ceramic layer 5 has a thickness 8 of less than approximately five microns for cost effective and efficient processing of orthopedic implants.

Figure 4:
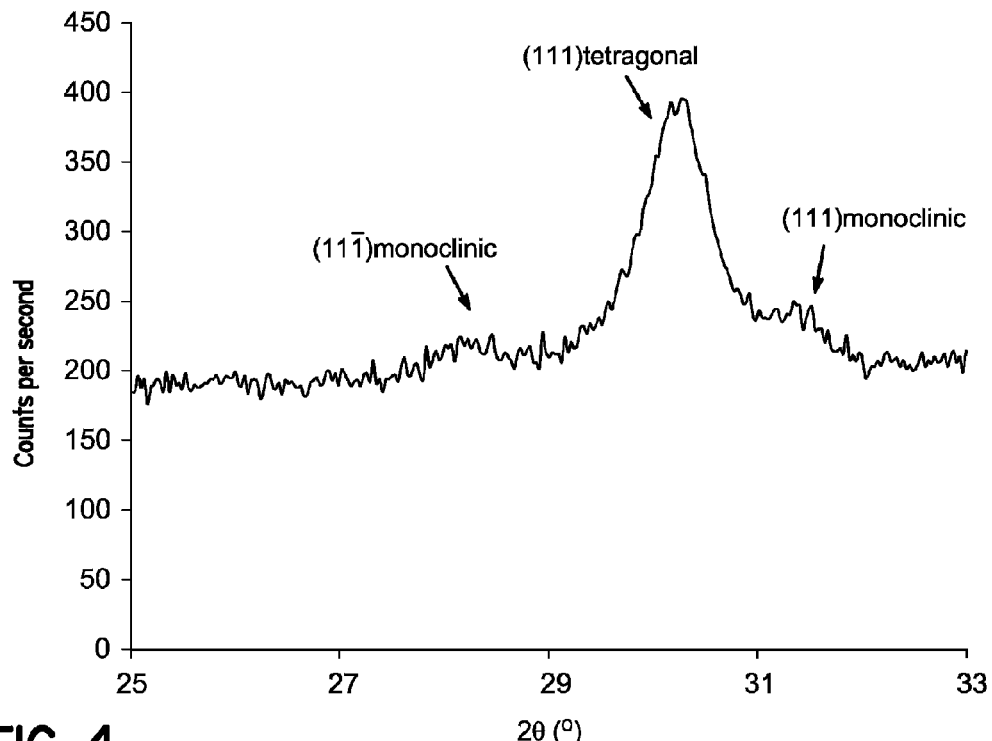
FIG. 4 is another illustration of an x-ray diffraction pattern of a zirconia ceramic layer deposited according to one embodiment of the present invention.

By way of example and not limitation, the desired structure was quantified with x-ray diffraction, as is known in the art. FIGS. 2, 4, and 5 are examples of x-ray diffraction data gathered from zirconia ceramic layers formed with one embodiment of the process of the present invention. A Scintag XDS 2000 x-ray diffractometer utilizing DMS 2000 software was used to gather the x-ray diffraction data. All scans were made in regular symmetric optics and a CuK-alpha radiation. An EG&G Ortec solid-state detector, model number GLP-10195/07-S was used to gather each x-ray diffraction pattern. Following phase identification, the relative volume of each crystal phase was determined by deconvoluting and peak fitting the x-ray diffraction patterns.

One method for quantifying the relative percentages of zirconia phases is with a method found in "Quantitative X-ray Diffraction Analysis of Polymorphic Mixes of Pure Zirconia," P. A. Evans, R. Stevens and J. G. P. Binner, Br. Ceram. Trans. J., vol. 83, pp. 39-43, 1984, incorporated by reference herein. As detailed in the article, the method uses the following equation to estimate the volume percent of each phase within the ceramic layer.

$$f_t = \frac{I_t(111)}{I_m(111) + I_m(11\bar{1}) + I_t(111)}$$

Where:
$f_t$ is a volume fraction of tetragonal zirconia
$I_t(111)$ is an integrated intensity of the tetragonal (111) peak
$I_m(111)$ is an integrated intensity of the monoclinic (111) peak
$I_m(11\bar{1})$ is an integrated intensity of the monoclinic (11$\bar{1}$) peak Ultimately, provided no cubic phase is detected, the fraction of monoclinic, $f_m$, is derived from $$f_m = 1 - f_t$$

To determine the various integrated intensities (e.g. $I_t(111)$, $I_m(111)$, $I_m(11\bar{1})$), background intensities were assumed to be linear over the narrow angular ranges used. The peaks were deconvoluted and fitted using a standard Pearson VII algorithm, as is known in the art.

As depicted in FIG. 2, in one exemplary x-ray diffraction pattern, the ceramic layer comprises both tetragonal and monoclinic zirconia. The ceramic layer has a $(11\bar{1})$ monoclinic diffraction peak and a (111) tetragonal diffraction peak indicating that the desired structure comprises two crystal phases of zirconia, i.e., a tetragonal zirconia and a monoclinic zirconia. Following peak fitting and deconvolution, the fraction of monoclinic, $f_m$, may be calculated. In turn, $f_m$ may be used to calculate a percent monoclinic. As depicted in FIG. 3, the "% Monoclinic" represents the ratio of the monoclinic zirconia to the tetragonal zirconia. As shown in TABLE 1, the % Monoclinic calculated from the x-ray diffraction pattern, shown in FIG. 2, is 20.0.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and process and illustrative examples shown and described. Accordingly, departures may be made from such details without departing from the scope of the general inventive concept.

What is claimed is:

1. An orthopedic implant comprising:
   an orthopedic body having a deposition surface; and
   a deposited ceramic layer supported by the deposition surface, the ceramic layer comprising two or more crystal phases comprising a monoclinic phase and a tetragonal phase having a volume ratio of greater than 0 to less than or equal to about 0.3, the two or more crystal phases sufficient to suppress phase transformation from the tetragonal phase to the monoclinic phase.

2. The implant of claim 1, wherein the deposited ceramic layer is formed on the deposition surface.

3. The implant of claim 1, wherein the ceramic layer comprises at least one polymorphic material.

4. The implant of claim 1, wherein the ceramic layer comprises $SiO_2$, $ZrO_2$, $TiO_2$, $AS_2O_3$, $CaTiO_3$, $Al_2SiO$, $BN$, $ZnS$, or $FeS_2$, or a combination thereof.

5. The implant of claim 1, wherein the ceramic layer comprises zirconia.

6. The implant of claim 1, wherein the ceramic layer comprises a zirconia ceramic layer having at least two of the two or more crystal phases.

7. The implant of claim 1, wherein the volume ratio of the monoclinic phase to the tetragonal phase is sufficient to suppress phase transformation from the tetragonal phase to the monoclinic phase.

8. The implant of claim 1, wherein the volume ratio of the monoclinic phase to the tetragonal phase suppresses phase transformation from the tetragonal phase to the monoclinic phase so as to not roughen due to a phase transformation during use in vivo.

9. The implant of claim 1, wherein the two or more crystal phases comprise a monoclinic zirconia having a plurality of oriented monoclinic crystals on the deposition surface, the oriented monoclinic crystals including more $(11\bar{1})$ monoclinic lattice planes than (111) monoclinic lattice planes.

10. The implant of claim 1, wherein the ceramic layer comprises zirconia comprising a monoclinic zirconia, a tetragonal zirconia, or a cubic zirconia, or a combination thereof.

11. The implant of claim 1, wherein the ceramic layer has a thickness of less than approximately 5 microns.

12. The implant of claim 1, wherein the ceramic layer is configured so as to not roughen due to a phase transformation during use in vivo.

13. The implant of claim 1, wherein an outer surface of the ceramic layer forms an articular surface.

14. The implant of claim 1, wherein the orthopedic body and the ceramic layer are configured for placement at an artificial joint.

15. The implant of claim 1, wherein the orthopedic body and the ceramic layer comprise a shape resembling a femoral hip ball or a femoral knee portion.

16. An artificial joint comprising:
   an orthopedic body having a deposition surface; and
   a deposited ceramic layer having a thickness of less than 5 microns and positioned on the deposition surface, the ceramic layer including at least a monoclinic zirconia phase and a tetragonal zirconia phase in a volume ratio of greater than 0 to less than or equal to about 0.3 and sufficient to suppress phase transformation from the tetragonal phase to the monoclinic phase, wherein the phase transformation suppression is in an amount sufficient to inhibit roughening of the ceramic layer during use in vivo;
   wherein an outer surface of the ceramic layer is configured as an articular surface.

17. An artificial joint comprising:
   an orthopedic body having a deposition surface; and
   a deposited ceramic layer having a thickness of less than 5 microns and positioned on the deposition surface, the ceramic layer including at least a monoclinic zirconia phase having a plurality of oriented monoclinic crystals, the oriented monoclinic crystals comprising more $(11\bar{1})$ monoclinic lattice planes than (111) monoclinic lattice planes, wherein the orientation of the monoclinic crystals is sufficient to suppress phase transformation to the monoclinic phase, wherein the phase transformation suppression is in an amount sufficient to inhibit roughening of the ceramic layer during use in vivo;
   wherein an outer surface of the ceramic layer is configured as an articular surface.

* * * * *